United States Patent [19]
Mehl et al.

[11] Patent Number: 4,566,454
[45] Date of Patent: Jan. 28, 1986

[54] SELECTED FREQUENCY HAIR REMOVAL DEVICE AND METHOD

[75] Inventors: Thomas L. Mehl, 1961 SW. 56th Ave., Plantation, Fla. 33317; William S. Burdick, Kissimmee, Fla.

[73] Assignee: Thomas L. Mehl, Pompano Beach, Fla.

[21] Appl. No.: 274,270

[22] Filed: Jun. 16, 1981

[51] Int. Cl.⁴ ............................................. A61B 17/41
[52] U.S. Cl. ........................... 128/303.13; 128/303.17
[58] Field of Search ...................... 128/303.13, 303.14, 128/303.17, 303.18, 303.19

[56] References Cited

U.S. PATENT DOCUMENTS

| 3,054,405 | 9/1962 | Topper | 128/303.18 |
| 3,804,096 | 4/1974 | Gonser | 128/303.14 |
| 3,815,603 | 6/1974 | Sramek | 128/303.18 |
| 3,875,945 | 4/1975 | Friedman | 128/303.14 |
| 3,999,552 | 12/1976 | Huggins | 128/303.13 |
| 4,321,926 | 3/1982 | Rose | 128/303.18 |

FOREIGN PATENT DOCUMENTS

| 2383675 | 11/1978 | France | 128/303.13 |
| 1513057 | 6/1978 | United Kingdom | 128/303.13 |

Primary Examiner—Lee S. Cohen
Attorney, Agent, or Firm—Shlesinger Arkwright Garvey & Fado

[57] ABSTRACT

Radio frequency energy is applied to a hair at a selected frequency at which that hair impedance to RF energy conduction is substantially lower than at other RF frequencies, to thereby obtain substantially greater energy conduction capability along the hair shaft to the hair papilla.

21 Claims, 10 Drawing Figures

SELECTED FREQUENCY HAIR REMOVAL DEVICE AND METHOD

BACKGROUND OF INVENTION

This invention relates to a radio frequency hair removal device and method for removing unwanted hair more effectively and permanently impairing future hair regrowth.

The most recent and more popular type of hair removal or epilator device that is currently in use is a tweezer type unit, through which RF energy is applied to the hair shaft. An example of one such device is shown in the Mehl U.S. Pat. No. 4,174,713.

This device is a hand-held tweezer type instrument to which radio frequency is applied. The hair is grasped between the tweezer tips and RF energy focused on the hair, through which it travels down to the hair papilla.

One of the important factors in effectiveness of such a device is the amount of RF energy that can be carried within the hair shaft and down to reach the hair papilla area at the hair shaft base. Ordinarily, the radio frequency energy is applied at a voltage of 100 to 300 peak to peak volts and has a frequency of 13.1, 27.1, or 40 megahertz. This radio frequency energy applied through the tweezer of the device shown in the Mehl U.S. Pat. No. 4,174,713 will usually bring about release and removal of the hair with damage to the hair papilla within two to ten seconds after RF energy is applied. This treatment time can be substantially reduced, or, the voltage itself greatly reduced, if the radio frequency which is applied to the hair is a frequency (resonant frequency) at which the particular hair has a reduced impedance to conduction of radio frequency energy. It has been found that the application of such a resonant frequency to the hair will substantially lower the voltage required to effect release and removal of the hair, and will still cause substantial damage to the hair papilla area.

SUMMARY AND FEATURES OF INVENTION

Accordingly, this invention contemplates a device and method for removing hair more effectively in which the principle of finding and selecting a resonant frequency for a given hair is used to reduce the hair's impedance to RF energy, thereby shortening time required for removal of the hair or to permit substantially reducing the amount of voltage required for hair removal.

Another feature of this invention is to provide a device and method in which the impedance of the hair to RF energy conduction is lessened.

It is a still further feature of this invention to provide for more effective removal of hair by providing for improved transmission of RF energy to the hair papilla area.

It is yet another object of this invention to apply plural radio frequencies to a particular hair to find the radio frequency for that at which it more readily conducts RF energy to the hair papilla, and to apply this frequency at a higher voltage to the hair for more effective hair removal.

It is a still further feature of this invention to provide an epilator device which can operate on low power, and will have substantially less RF radiation than prior devices.

Another feature of this invention is to make it possible for a tweezer device to effectively operate on low voltage and on battery power.

A still further feature of this invention is to make it possible for a tweezer device to operate effectively on many frequencies without change of transmission cable length.

A yet further object of this invention is to provide greater safety with respect to use of the unit, in that it can be operated at lower radiation levels and that it operates at lower voltage levels.

These and other objects and features of this invention will be apparent from the following description and claims.

DESCRIPTION OF THE INVENTION

Figure 1:
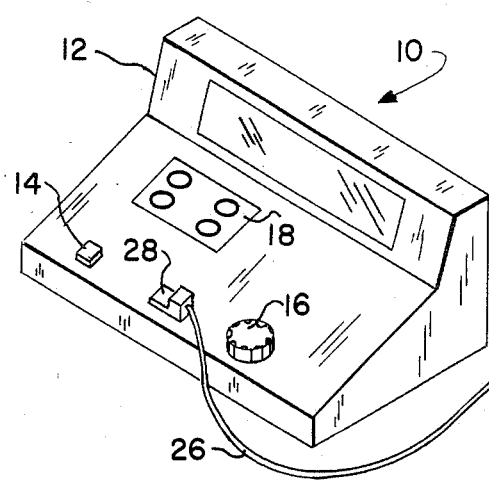
FIG. 1 is a perspective view of an epilator device which uses present techniques.

Referring to FIG. 1, the present unit generally indicated at 10, has a housing 12 with an on/off button 14, an adjustable voltage control knob 16, and frequency selection buttons on panel 18.

The hand-held tweezer implement generally indicated at 20 has tweezer tips 22 extending out the forward end of the implement, and a tweezer grasping and RF voltage control button 24. The tweezer implement 20 is connected to the housing 12 through the coaxial cable 26 which supplies the radio frequency energy to it through connecting plug 28.

Figure 2:
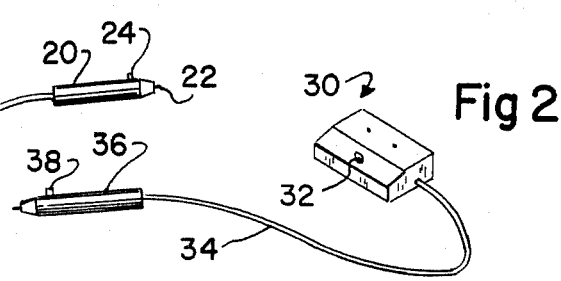
FIG. 2 is a view of an epilator device of substantially smaller size and which is battery operated, using the techniques of this invention.

Referring to FIG. 2, the battery operated unit generally indicated at 30 has a power indicating light 32, a connecting coaxial cable 34, and a hand-held tweezer implement housing 36 which has a tweezer and power control button 38. The design of these units tweezer hand-held implements is similar to that shown in Mehl U.S. Pat. No. 4,174,713.

Figure 3:
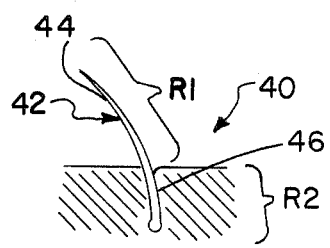
FIG. 3 is a cross-sectional view of skin tissue showing an actively growing hair.

The electrical characteristics which have been discovered and are used in conjunction with this invention are illustrated in FIGS. 3 through 7. In FIG. 3, a hair in position in a tissue is generally indicated at 40. The hair shaft 42 has a free upstanding section 44 which is disposed above the skin level and has a resistance R1, the lower hair section 46 below the skin level and extending to the papilla has a higher resistance R2. The total resistance of hair 42 from the outer tip to the papilla at the base end of the hair 42 is R1+R2. The uppermost section of the hair 44 has a higher resistance R1 in that it has less oils and moisture than the hair section 46 below the skin. This is one of the reasons why it is desirable to engage the hair shaft 42 as close to the skin level as possible to reduce the length of the resistance R1.

Figure 4:
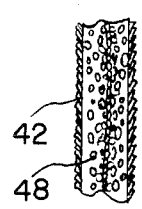
FIG. 4 is an enlarged sectional view of a hair shaft.

FIG. 4 shows a portion of the hair 42 greatly magnified showing small particles 48 of coloring material which are distributed throughout the hair, but primarily concentrated near the center of the hair shaft. These particles are iron and of metallic compounds which give the hair color. It is believed that these elements give the hair shaft RF conducting capability and, inasmuch as they are concentrated near the center of the hair shaft, provide a central interior conducting path for the RF energy. For the most part, they are scattered and do not directly contact one another. It is believed that they act as small capacitive conductive plates.

Figure 5:
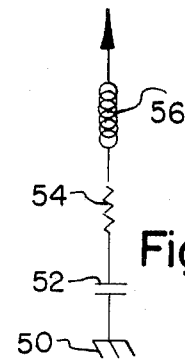
FIG. 5 is an equivalent electrical circuit for a typical hair.

FIG. 5 is an equivalent electrical circuit of the hair showing it grounded at 50 and containing a capacitive element 52, a resistive element 54, and an inductive element 56 in series. At low frequencies this equivalent electrical model indicates the hair should be a poor conductor, and that the conducting capability should increase as the frequency increases until a maximum conducting frequency value, termed a resonant frequency, will occur. At this frequency, conduction will be a maximum and impedance to RF energy conduction will be a minimum. The impedance of this model is high at low frequencies because the capacitance is very small. At the series resonant frequency larger RF current will be carried down the hair shaft. It should be noted that the values of each of these elements of the equivalent circuit will vary with each individual characteristic and type. Therefore the frequency at which it more effectively conducts RF energy (its resonant frequency), will vary with each hair. However, different hair types can be grouped and a typical frequency for that type of hair applied.

It is known that red hair, for example, is more effectively removed in a shorter period of time than other types of hair, such as coarse gray hair. Red hair has a very high metallic compound particle density and consequently it is believed more effectively conducts RF energy, since the value of the resistive element 54 will be lower than for the other types of hair.

Figure 6:
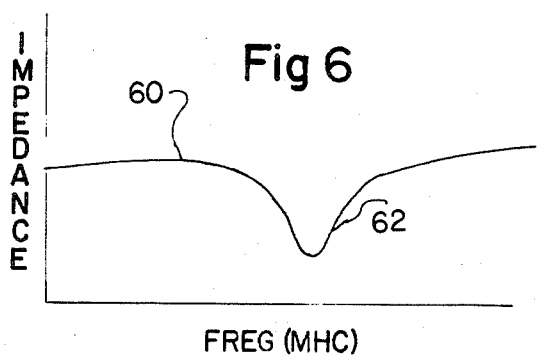
FIG. 6 is an impedance versus frequency curve for hair.

FIG. 6 is a resistance/frequency diagram illustrating the effect of frequency on resistance of the hair to RF energy conduction. The curve at 60 gradually descends until at the resonant frequency in the area 62 of the curve, the resistance is a minimum. It is at this frequency that resistance to RF conduction is a minimum (the resonant frequency).

Figure 7:
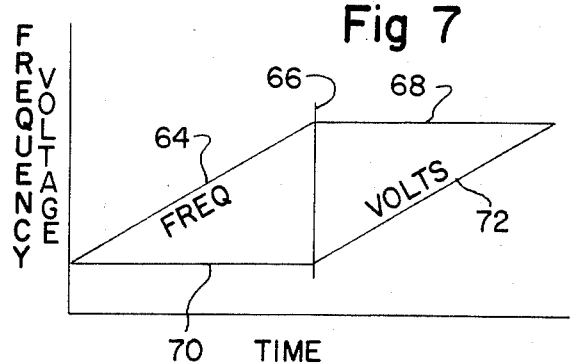
FIG. 7 is a graph showing frequency and voltage curves as a function of time for a hair.

FIG. 7 shows a frequency versus time curve 64 illustrating that as frequency and time increase the curve rises to resonance at the line 66. This shows the low frequency value initially applied rises through the initial part of the sweep until the resonant frequency is reached at point 66. When this resonant frequency is reached, the frequency is maintained at that value along line 68.

The voltage versus time curve 70 shown on the same graph also illustrates what happens in the unit. A fixed low voltage on the order of one to ten volts is initially applied until the resonant frequency value is determined at line 66, and then the voltage is increased as shown at 72, keeping the frequency the same to conduct maximum RF energy down the hair shaft.

The frequency range for application will cover from approximately one to ten volts initially during the radio frequency sweep for a line current unit, and the voltage will be increased to 100 to 200 volts after the resonant frequency is reached. For a battery unit, the initial sweep voltage value will be approximately one to three volts, and the resonant frequency voltage applied is from nine to thirty volts.

Figure 8:
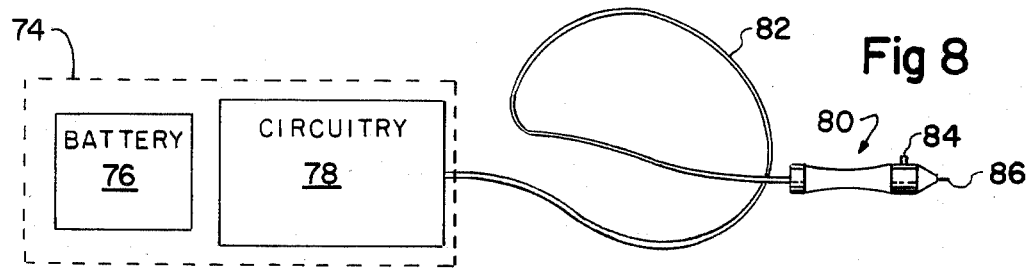
FIG. 8 shows the portable unit of FIG. 2 of the present invention.

The major components of the small battery powered hair removal device of FIG. 2 is shown in FIG. 8. The housing 74 has two major components. A battery section 76 and an instrumentation section 78 are shown in block form. The hand-held tweezer device generally indicated at 80 is connected to the housing 74 by the coaxial cable 82. The tweezer unit 80 has a closing and activating button 84 which is depressed by the thumb of the person holding the unit, and at its front end has the tips of the two tweezer arms 86 projecting therethrough for grasping the hair.

Figure 9:
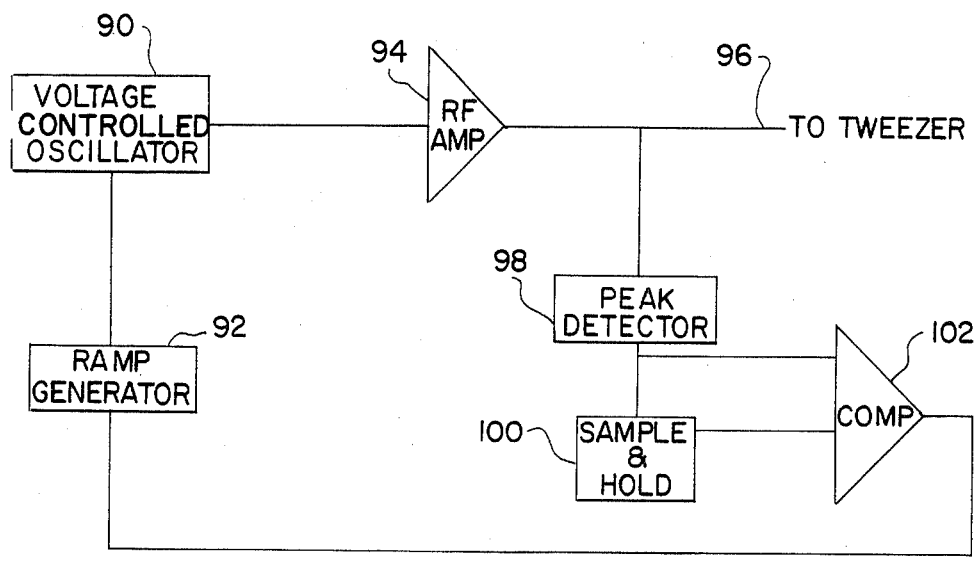
FIG. 9 is a block diagram of the major components of the frequency generating section of the epilator of FIG. 8.

FIG. 9 is a block diagram of the radio frequency generating circuit used to sweep the frequency range. A voltage controlled oscillator 90 has its output varried in accordance with the continuously changing voltage supplied thereto through the ramp generator 92 when the circuit is sweeping for the resonant frequency. This variable frequency output is necessary since the resonant frequency for each hair will vary. Previously, the standard operating RF frequency for these devices was 27.1 MHZ. But with the discovery of substantially better results in removal with RF applied at resonant frequency values, it is necessary to vary the frequency from 1 to 200 MHZ. The ramp generator 92 accomplishes this by producing an increasing voltage output which results in changing the frequency values produced by the voltage controlled oscillator. This variable frequency is supplied to the radio frequency amplifier 94, the output of which is supplied along coaxial cable 96 to the tweezer.

A peak detector 98 is connected to the output of the radio frequency amplifier in parallel with line 96. The peak detector circuit senses a minimum impedance (maximum conduction). Its output is also in parallel with a lead connected to the comparator circuit 102. The output from the sample and hold circuit 100 is supplied to the second input of the comparator circuit 102.

As the frequency output from the radio frequency amplifier 94 increases, frequencies will be reached at which the impedance along line 96 will decrease due to the decreased hair impedance as the frequency reaches a value corresponding to the resonant frequency 62 of FIG. 6 beyond which impedance will again climb. As soon as the impedance begins to go up, the increase will be noted in the comparator circuit 102 which will send a control signal for the ramp generator 92, fixing its output so that from then on a fixed voltage is applied to the voltage controlled oscillator 90, resulting in a fixed frequency being supplied to the RF amplifier 94.

At this time, a control line (not shown) connected to the amplifier brings about an increase of the voltage level from the RF amplifier 94 to produce a higher voltage output at this resonant frequency. Prior to the receipt of the control signal from the comparator 102, the ramp generator output is a continuously ascending voltage signal which acts on the voltage controlled oscillator to increase its frequency output. When the hair is removed and the tweezer released, the ramp generator is reset so that with the next hair, it can begin its sweep from the low to high frequency values again.

Figure 10:
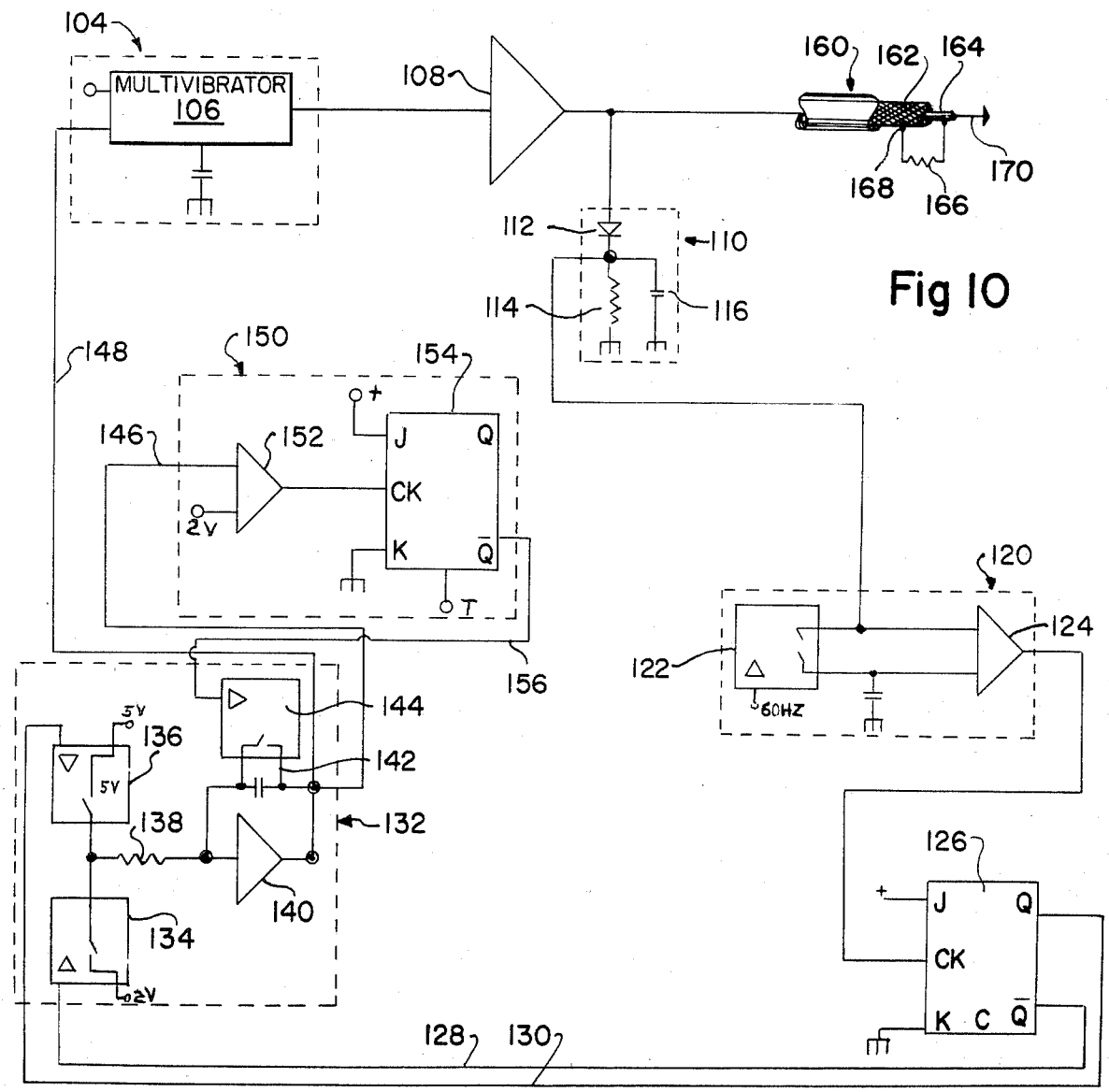
FIG. 10 is a schematic diagram showing the circuit elements of the circuit of FIG. 9.

The specific circuitry for the block diagrams of FIG. 9 is shown in FIG. 10. The voltage controlled oscillator 104 is a Fairchild 11C58 voltage controlled multivibrator 106 having an output of from 1 to 200 MHZ depending upon the input control voltage. The radio frequency amplifier 108 is made of discrete components and is a wide band amplifier that has variable gain and a band width of 1 to 200 MHZ. The peak detector circuit generally indicated at 110 includes a diode 112 and resistor 114 connected in parallel with capacitor 116. This circuit indicates whether the load is increasing or decreasing in impedance by converting the radio frequency amplifier voltage at its output to a DC voltage, so that a change in the radio frequency output will cause a drop in DC voltage at the common connection of the elements.

The peak detector circuit is connected to the comparator circuit at 120. The peak detector output line is connected in parallel with the MOS quad bilateral switch 122 (Fairchild 4016B) and to the comparator chip 124 (Fairchild UA710HC), where it is connected to the negative input line. As the frequency increases, the switch which is shorting sixty times a second approximately, and which has a small bias applied (not shown), keeps the lower input line (the positive one) above the negative value and the output will stay high. As soon as the resonant frequency is reached, the output from the detector will begin to increase, and the output of the comparator chip 124 will be lower. This lower output clocks the Flip-Flop chip 126 (Fairchild 4027 MOS J-K Flip-Flop), and the Q output goes high, while the $\bar{Q}$ output goes low. With the change, the sweep of the ramp generator is stopped.

The output from the flip-flop 126 is carried to the ramp generator circuit 132 along lines 128 and 130 to the two quad bilateral switches (Fairchild 4016B). During the sweep, the top switch 136 (connected to a 5-volt supply) is shorted, and the lower switch 134 (connected to a 2-volt supply) is opened. They have a common connection through resistor 138 to the negative input line of operational amplifier chip 140 (Fairchild UA741TC). Its positive input is 2 volts, and during the frequency sweep it acts an an integrator, with the output voltage steadily increasing. At lock-on, (when Q of 126 goes high) the top switch opens, and the bottom switch 136 shorts, reducing the current output into the amplifier 140 to nearly zero, stopping the action of the ramp circuit and holding the output at a constant voltage. This output voltage goes to the voltage controlled oscillator circuit 104 along line 148.

The circuit 150 is a resetting circuit for the ramp generator. Lines 142 and the MOS analog switch 144 bridge the amplifier's feedback line through its capacitor when it is shorted by a signal from the resetting circuit 150. This circuit is responsive to the tweezer which is connected to chip 154 (Fairchild 4027PC). Amplifier 152 is responsive to output from amplifier 140 and feeds flip-flop 154, the $\bar{Q}$ output of which is connected along line 156 to switch 144. The tweezer reset control is connected to chip 154 at terminal T.

An input line (not shown) is connected between the Q output of the flip-flop chip 126 and at the amplifier 108 to increase the amplifier output voltage when comparator 124 activates the Q output as the resonant frequency for that hair is reached.

The object of using a low voltage of 1 to 5 volts, rather than a higher voltage, is to permit finding the proper resonant frequency without destroying the hair beforehand. After the resonant frequency is found, the voltage is increased to transmit full RF energy at that frequency to the papilla. The lowest impedance results in maximum transmission to RF to the papilla. The papilla should receive a maximum dose of energy before the hair which carries the RF energy to the papilla breaks off from it and releases.

The voltage controlled oscillator 106 is reset to the low frequency value after the hair is released, in preparation for the next sweep circuitry. The voltage controlled oscillator has a 10 pf capacitor connection to ground.

Within this circuit, the resonant frequency for the hair being treated actually triggers the circuit as the resonant frequency is approached, inasmuch as the circuit becomes more loaded, bringing down the voltage output from the amplifier. The drop in amplifier output affects the sample circuit which acts as an integrator, and the logic circuits responding to its output stops the frequency sweep of the voltage controlled oscillator and turns up the gain of the radio frequency amplifier.

The property of the hair of changing impedance depending upon the radio frequency applied is the basis for the operation of the above-described circuit. It is believed that the equivalent circuit of the hair is a series RLC circuit in which the resonant frequency minimizes impedance. At this frequency the load through the hair and on the circuit will be a maximum, and is sensed as described above.

The actual construction of the hair itself supports the theory of its equivalent circuit being an R-L-C circuit. The hair granules which are small conductors of sorts are spaced throughout the hair length, although more densely concentrated at the center of the hair. They act as tiny conductors which are encased by insulative material so that there is a capacitor-like plate construction. In addition, the granules have an axial length in the direction of the radio frequency path so that they will also act as small inductors. The makeup, orientation and spacing of these particles and the thickness of the hair shafts vary from hair-to-hair so that the frequency at which a given hair presents the lowest impedance to radio frequency energy will vary.

Another aspect of this invention, which makes it possible to effectively conduct different frequencies through the same length of coaxial cable, is shown at the top of FIG. 10. The tweezer is supplied with power through the coaxial cable, generally indicated at 160, which is connected at its other end to the output of the radio frequency amplifier 108. Ordinarily, in tweezer-type hair removal units, the length of the coaxial cable connecting the radio frequency generator to the tweezer is of a fixed preselected length which depends upon the particular frequency being transmitted through the cable. The length is chosen as one-quarter of the frequency wave length being transmitted to provide maximum voltage (maximum voltage standing wave ratio) at the tweezer. An important aspect of this invention is to avoid this formerly used constraint of a fixed one-quarter length of coaxial cable for a given frequency applied. A fixed length cable is obviously not effective in a unit that employs variable frequencies. Therefore, the use of any coaxial cable length for a given frequency free from this constraint, is an important aspect of this circuit. This is accomplished by matching the impedance of the coaxial cable with an independent impedance to ground connected in parallel with the end of the coaxial cable and the tweezer input. In this instance, the antenna is considered to be a tweezer, rather than the coaxial cable, and the matching impedance minimizes voltage standing wave ratio in the coaxial cable.

As shown in FIG. 10, the impedance match is accomplished through the use of a parallel impedance connection to ground at the point 170 that the tweezer and coaxial cable are joined. Ordinarily, the length of coaxial cable has an impedance of 50 ohms, and consequently the grounding impedance value should be 50 ohms.

Alternatively, a transformer can be used to match the tweezer impedance to that of the coaxial cable. The primary coil is connected as the impedance to ground with the secondary connected to ground at one end and to the tweezer at the other. Alternatively, a resistor having a tap can be connected at one end 168 to the grounding sheath 162 of the cable and to end 170 and the tweezer at the other, with the tap connected to the coaxial cable. The value of the impedance 166 between the coaxial cable central conductor 164 and to ground would match the impedance of the entire coaxial cable length.

OPERATION

To operate the units of FIGS. 1 and 2, the user grasps the epilator instrument 24 or 36 and grasps the hair to be removed between the tweezer device which is of the type shown in the Mehl U.S. Pat. No. 4,174,713.

In the device illustrated in FIGS. 8 through 10, as soon as the activating button is pressed, the circuitry provides radio frequency energy at low frequency which progressively increases in value until a dip in impedance is noted by the voltage peak detector circuit 98 of FIG. 9, at which time the sweep is discontinued and the radio frequency energy at this frequency is applied thereafter to the hair grasped and held between the tweezer. This frequency is the resonant frequency at which the impedance of the hair to passage of radio frequency energy is lowest for that type of hair. Once the resonant frequency is found, the voltage can also be increased to expedite hair removal by applying more energy. This decreases the time required for release of the hair.

The frequency range is preferably between 1 to 200 megacycles. The finer, blonde-type hair will have a resonant frequency at values of from approximately 1 to 15 megahertz. Red hair has a resonant frequency within the range of 25 to 40 megahertz, and black, heavy, or gray hair has a resonant frequency in the range from 75 to 150 megahertz, approximately. The sweep circuit will find the exact frequency for a given hair and stop at that frequency which will be located within the ranges for the particular hair in question. This is the preferable and more exact approach to finding the resonant frequency at which the exact value is determined.

It is also possible to directly select a frequency for a given type of hair, such as thick, thin, gray, black, blonde, or red hair. In FIG. 1 the panel 18 shows four frequency selection buttons which can be used for this purpose. However, the frequency will only be approximately that of the resonant frequency and will not give the results of the sweeptype circuit.

With the use of the resonant frequency circuit, it is possible to obtain almost immediate results after application of the radio frequency energy at the resonant frequency to the hair. Instead of a release time of ten to twenty seconds, the release time is substantially reduced and, in some instances, may almost be so short as to be considered instantaneous. Release time is the period of time required from initial application of radio frequency energy to the time that the hair actually can be removed. Release occurs when the papilla area at the hair root is badly damaged and the hair breaks clear of the papilla. A slight pop-up movement of the hair at the skin is usually observable, after which the hair can readily be slid out of the skin with so little resistance that in most cases it is not felt by the person being treated.

It is believed that the application of radio frequency energy at the resonant frequency substantially reduces the impedance of the hair, making it possible to substantially damage the hair papilla prior to release. This is accomplished much more rapidly than previously where only one standard fixed frequency which was not resonant for a given hair was applied to all types of hair.

Because it is easier to transmit radio frequency energy through the hair at a resonant frequency, it is possible to substantially reduce the voltage of the radio frequency energy applied. Consequently, one important and significant result of this lowered voltage requirement is to permit use of the lower powered unit that requires only a small battery, and can be portable, rather than the previously used line-current type unit requiring high voltage and power consumption.

This discovery of reduced hair impedance at various resonant frequencies, depending upon the type of hair, is apparently due to the electrical property of the hair itself, as indicated in FIG. 5 in which the equivalent electrical circuit is shown with capacitive, resistive, and inductive elements in series. The values of each will vary with respect to the type of hair under consideration. This electrical equivalent circuit of a hair shaft is substantiated by the discovery of reduced hair impedance at various frequencies depending upon type of hair.

Although resistance is high, and hair ordinarily is considered as a non-conductor, these results show that when radio frequency energy of the right voltage and frequency are applied directly to a hair shaft, and in a focused manner as described in the Mehl U.S. Pat. No. 4,174,713, there is conduction down the hair shaft, even though it has a high resistance.

It is believed that this ability of hair to conduct down through what is believed to be the central part of the hair is the result of the granules in the hair itself, and their arrangement which make it possible for this type of radio frequency energy to travel along the central part of the hair shaft directly to the papilla area.

While this invention has been described, it will be understood that it is capable of further modification, uses and/or adaptations of the invention following in general the principle of the invention and including such departures from the present disclosure as come within known or customary practice in the art to which the invention pertains, and as may be applied to the essential features hereinbefore set forth, as fall within the scope of the invention or the limits of the appended claims.

What is claimed is:
1. A hair removal device, comprising:
 (a) radio frequency energy applying means for conveying radio frequency energy to a hair for conduction to the hair papilla
 (b) radio frequency energy generating means connected to the radio frequency applying means for producing radio frequency energy at a given frequency and voltage, and

(c) radio frequency selection means connected to the radio frequency energy generating means and to the radio frequency applying means for providing a radio frequency scan over a wide range of hair conduction frequencies and finding a frequency at which the impedance of a given hair to transmission of radio frequency energy at that frequency is substantially lower than for the other radio frequencies in that frequency range.

2. The hair removal device as set forth in claim 1, wherein:
(a) the radio frequency selection means includes radio frequency sweep control means for varying the output of the radio frequency energy generating means over a preselected range of frequencies to find and apply the radio frequency at which the hair impedance is substantially less than for the other radio frequencies in the range.

3. The hair removal device as set forth in claim 2, wherein:
(a) the radio frequency sweep control means determines and applies the resonant frequency for the hair being removed.

4. The hair removal device as set forth in claim 2, wherein:
(a) the radio frequency energy generating means includes means for providing a low voltage output during the course of the sweep of frequencies, and a substantially higher voltage output for the frequency where the hair impedance is substantially less than at other frequencies.

5. The hair removal device as set forth in claim 4 wherein:
(a) electrical circuit means is connected with the radio frequency energy applying means and the radio frequency generating means to minimize the voltage standing wave ratio in the radio frequency energy applying means, and
(b) a battery is connected to the radio frequency energy generating means as the power source.

6. The hair removal device as set forth in claims 1 or 2, wherein:
(a) electrical circuit means is connected with the radio frequency energy applying means and the radio frequency generating means to minimize the voltage standing wave ratio in the radio frequency energy applying means.

7. The hair removal device as set forth in claim 1 or claim 2, wherein:
(a) a battery is connected to the radio frequency energy generating means as the power source.

8. The hair removal device as set forth in claim 2, wherein:
(a) the radio frequency sweep control means includes variable frequency generating means and a sensing and control circuit connected to the radio frequency energy applying means for providing a control signal dependent upon the electrical load on the radio frequency generating means.

9. The hair removal device as set forth in claim 8, wherein:
(a) the radio frequency energy applying means includes an electrical tweezer which is supplied with radio frequency energy through a coaxial cable connected to the radio frequency energy generating means, and
(b) electrical means connected in parallel with the coaxial cable and includes a ground impedance having the same value as the impedance of the coaxial cable which is connected at the junction of the tweezer and the coaxial cable.

10. The hair removal device as set forth in claims 1, 2, 5 or 9, wherein:
(a) the radio frequency energy generating means produces radio frequencies in the range of from 1-200 Megahertz.

11. The hair removal device as set forth in claim 1, wherein:
(a) the radio frequency selection means includes an electrical element for setting the output frequency at one of a plurality of different frequencies so that the more effective frequency for a given type of hair may be selected.

12. The hair removal device as set forth in claim 1, wherein:
(a) electrical circuit means is connected with the radio frequency energy applying means and the radio frequency generating means to minimize the voltage standing wave ratio in the radio frequency energy applying means, and
(b) a battery is connected to the radio frequency energy generating means as the power source.

13. A hair removal device, comprising:
(a) a hand-held electrical tweezer for applying radio frequency energy to a hair which is to be removed,
(b) variable radio frequency energy generating means for supplying radio frequency energy to the tweezer at different frequencies,
(c) a length of coaxial cable connecting the tweezer and the radio frequency energy generating means,
(d) electrical circuit means electrically connected with the tweezer and the radio frequency generating means for minimizing the voltage standing wave ratio in the tweezer,
(e) electrical sensing means connected in circuit with the radio frequency energy generating means for sensing the frequency at which the hair has minimum impedance to radio frequency energy, and producing a control signal when such condition occurs, and
(f) the variable frequency generating means including a control circuit for producing frequencies within the range of 1 to 200 Megahertz, and being responsive to the control signal for maintaining the sensed frequency at which the hair has minimum impedance to radio frequency energy.

14. The hair removal device as set forth in claim 13, wherein:
(a) the radio frequency generating means includes a voltage controlled oscillator, the output of which is supplied to a power amplifier,
(b) the electrical sensing means includes a peak detector and logic circuit connected to the output of the power amplifier and which generate the control signal, and
(c) a ramp generator is connected to the voltage controlled oscillator to control its frequency output, and is connected in circuit with the output of the logic circuit to receive the control signal.

15. A hair removal device, comprising:
(a) radio frequency energy applying means including an electrical tweezer connected to a coaxial cable for conveying radio frequency energy to a hair for conduction to the hair papilla,
(b) radio frequency energy generating means connected to the coaxial cable of the radio frequency energy applying means for producing radio frequency energy at a given frequency and voltage, (c) electrical conducting means connected in parallel circuit with the coaxial cable of the radio frequency energy applying means and including a grounded impedance having the same value as the impedance of the coaxial cable connected at the junction of the tweezer and the coxial cable for reducing the voltage standing wave ratio in the radio frequency energy applying means.

16. A hair removal device, comprising:
    (a) radio frequency energy applying means including an electrical tweezer and a connecting coaxial cable for conveying radio frequency energy to a hair for conduction to the hair papilla,
    (b) radio frequency energy generating means connected to the electrical tweezer through the coaxial cable of the radio frequency energy applying means for producing radio frequency energy over a sweep range of radio frequencies,
    (c) electrical means connected with the radio frequency energy generating means for providing a low voltage output from the radio frequency energy generating means during the course of the sweep range, and a substantially higher output voltage for that frequency where the hair impedance is substantially less than at other frequencies.

17. A method for removing hair, comprising the steps of:
    (a) grasping the hair to be removed at a point adjacent the skin surface with a radio frequency energy transmitting tweezer,
    (b) selecting and applying successive radio frequency energy values which are in the range of from 1 to 200 Megahertz to the tweezer for transmission to the hair;
    (c) determining the frequency within such range at which the hair impedance is substantially less than for other frequencies,
    (d) applying voltage at such frequency through the tweezer to the hair for a period of time, and
    (e) removing the hair by withdrawing the tweezer from the skin surface.

18. The method for removing hair as set forth in claim 17, including the step of:
    (a) applying the lower impedance frequency to the hair at a substantially higher voltage than the voltage applied for the other frequencies.

19. A method for removing blond hair with a radio frequency tweezer hair removal device, comprising:
    (a) setting the hair removal radio frequency tweezer output frequency to a frequency range of from 1 to 15 Megahertz,
    (b) grasping a blond hair to be removed with the preset radio frequency hair removal tweezer for transmitting such radio frequency to the hair, and
    (c) applying sufficient radio frequency energy to the tweezer at a frequency within the frequency range of from 1 to 15 Megahertz at which the impedance of the blond hair to transmission of radio frequency energy is at a minimum to bring about removal of the blond hair.

20. A method for removing red hair with a radio frequency tweezer hair removal device, comprising:
    (a) setting the hair removal radio frequency tweezer output frequency to a frequency range of from 25 to 40 Megahertz,
    (b) grasping a red hair to be removed with the preset radio frequency hair removal tweezer for transmitting such radio frequency to the hair, and
    (c) applying sufficient radio frequency energy to the tweezer at a frequency within the frequency range of from 25 to 40 Megahertz at which the impedance of the red hair to transmission of radio frequency energy is at a minimum to bring about removal of the red hair.

21. A method for removing black hair with a radio frequency tweezer hair removal device, comprising:
    (a) setting the hair removal radio frequency tweezer output frequency to a frequency range of from 75 to 150 Megahertz,
    (b) grasping a black hair to be removed with the preset radio frequency hair removal tweezer for transmitting such radio frequency to the hair, and
    (c) applying sufficient radio frequency energy to the tweezer at a frequency within the frequency range of from 75 to 150 Megahertz at which the impedance of the black hair to transmission of radio frequency energy is at a minimum to bring about removal of the black hair.

* * * * *